United States Patent [19]
Willenborg et al.

[11] Patent Number: 5,159,412
[45] Date of Patent: Oct. 27, 1992

[54] OPTICAL MEASUREMENT DEVICE WITH ENHANCED SENSITIVITY

[75] Inventors: David L. Willenborg, Dublin; Allan Rosencwaig, Danville; Jon Opsal, Livermore, all of Calif.

[73] Assignee: Therma-Wave, Inc., Fremont, Calif.

[21] Appl. No.: 670,040

[22] Filed: Mar. 15, 1991

[51] Int. Cl.$^5$ ............................................. G01N 21/55
[52] U.S. Cl. .................................. 356/445; 356/448; 356/381; 356/355; 250/571
[58] Field of Search ............... 356/445, 446, 447, 381, 356/382, 355, 357, 448; 250/571

[56] References Cited

U.S. PATENT DOCUMENTS

| | | | |
|---|---|---|---|
| 4,831,276 | 5/1991 | Hyakumura | 356/445 |
| 4,984,894 | 1/1991 | Kondo | 356/381 |

Primary Examiner—Vincent P. McGraw
Assistant Examiner—LaCharles Keesee
Attorney, Agent, or Firm—Limbach & Limbach

[57] ABSTRACT

An approach for increasing the sensitivity of a high resolution measurement device 50 is disclosed. The device includes a laser 52 for generating a probe beam 54 which is tightly focused onto the surface of the sample 58. A detector 66 is provided for monitoring a parameter of the reflected probe beam. In accordance with the subject invention, a spatial filter is provided for reducing the amount of light energy reaching the detector that has been reflected from areas on the surface of the sample beyond the focused spot. The spatial filter includes a relay lens 68 and a blocking member 70 located in the focal plane of the lens. The blocking member 70 includes an aperture 72 dimensioned to block light reflected from the surface of the sample beyond a predetermined distance from the center of the focused spot. In this manner, greater sensitivity to sample characteristics within the highly focused spot is achieved.

13 Claims, 2 Drawing Sheets

OPTICAL MEASUREMENT DEVICE WITH ENHANCED SENSITIVITY

TECHNICAL FIELD

The subject invention relates to an approach for improving the sensitivity of a high resolution optical measurement apparatus.

BACKGROUND OF THE INVENTION

There has been significant interest in developing high resolution, non-contact optical measurement devices This interest is particularly acute in the semiconductor manufacturing industry where process steps are performed on a very small scale.

One example of a high resolution optical measurement device is described in U.S. Pat. No. 4,999,014, issued Mar. 12, 1991 assigned to the same assignee as the subject invention and incorporated herein by reference. This device is designed for measuring the thickness of a thin film layer on a substrate.

FIG. 1 is an illustration of the relevant portions of the above referenced device 10. Device 10 includes a laser 12 for generating a probe beam 14. A beam splitter 16 is used to redirect the beam down through a microscope objective lens 20 having a high numerical aperture. The lens 20 focuses the probe beam to a spot on the surface of the sample 18. The diameter of the spot is on the order of one micron. A stage 22 is provided to scan the sample with respect to the focused probe beam.

A photodetector 26 is provided to measure the probe beam after it has reflected off the surface of the sample. A relay lens 28 is provided to expand and image the beam on the detector. Detector 26 includes an array of individual detector elements capable of measuring the areal intensity of various rays as a function of their position within the reflected probe beam. The position of the rays within the beam correspond to specific angles of incidence with respect to the surface of the sample. A processor (not shown) derives the thickness of the thin film layer based on the angular dependent intensity measurements.

In the preferred embodiment, a second photodetector 34 is provided and arranged in a similar optical position as detector 26. A lens 36 is provided to image the beam on the detector 34. This second detector 34 is underfilled and configured to measure the full power of the reflected probe beam. The output from detector 34 is used to enhance the sensitivity of the evaluation.

In the arrangement discussed above, it would be expected that the light reaching either of the detectors 26 or 34 would be limited to that which has been reflected off the surface of the sample from within the focused spot. In practice, it has been found that some small amount of the light falling on the detectors has been reflected off the sample from areas outside of the focused spot. This light consists of portions of the probe beam that have been scattered or deflected out of the primary beam path. Such scattering effects can be produced by particulates in the air or on the lens. This effect can also be the result of imperfections in the lens or even in the beam itself. Experiments have shown that light energy can be measured by the detectors 26 and 34 from areas as far as 20 to 30 microns away from the edge of the focused spot. Since the device is intended to evaluate sample parameters only in the small one micron region, light reflected from areas outside the focused spot can improperly skew the measurement results.

While the amount of scattered light detected is relatively low, it is nonetheless significant. For example, changes on the order of 1 in 10,000 must be distinguished when measuring the full power of the reflected beam. Thus, even minor amounts of scattered light reaching the detector can adversely affect the analysis of the sample. Therefore, it would be desirable to provide an approach which can reduce the effects of light which has been reflected from areas outside of the focused spot.

The subject invention is not limited to the apparatus described in the above cited application but might be used in any optical device where high resolution and high sensitivity are required. One example of another type of device where the subject invention could be utilized is described in U.S. Pat. No. 5,042,951, issued Aug. 27, 1991 assigned to the same assignee as the subject invention and incorporated herein by reference.

The apparatus described in the latter application is an ellipsometric device which has a configuration similar in many respects to the device shown in FIG. 1 herein. The principle difference is that the detector system is arranged to analyze the change in polarization state of various rays within the probe beam as a result of its reflection off the sample surface.

There are a number of approaches found in the prior art for detecting the change in the polarization state of a probe beam. In its basic form, the apparatus will be provided with a polarizing section 40 (shown in phantom line) and an analyzing section 42 (also shown in phantom line). The polarizing and analyzing sections can include polarizing elements which can be rotated about the propagation axis of the beam. By knowing the relative azimuthal positions of these rotatable elements in conjunction with the intensity measurement of detector 26, the change in polarization state of the beam can be determined. The latter analysis will also be adversely affected by detected light that has been reflected off the sample surface from areas outside of the focused probe beam spot.

FIG. 1 illustrates one additional photodetector 46. Photodetector 46 is arranged to a measure a small portion of the probe beam that is transmitted through beam splitter 16. This portion of the light has not passed through lens 20 nor has it been reflected from the sample. The output of detector 46 is intended to monitor fluctuations in the output power of laser 12. The signal generated by detector 46 is used to normalize the output signals from detectors 26 and 34. In order to obtain an accurate normalization signal, it is necessary to insure that the portion of the probe beam striking detector 46 is the same as that which is passed through the aperture of the lens 18 to the sample. An approach for achieving that goal is also discussed below.

SUMMARY OF THE INVENTION

In accordance with the subject invention, an approach is provided to reduce the amount of detected light energy that has been reflected from a sample beyond the focused spot of the probe beam. The subject invention is implemented in an optical measurement apparatus which includes a laser for generating a probe beam. A high numerical aperture lens is provided for focusing the probe beam to a spot size of about one micron on the surface of the sample. A detector is provided for measuring some parameter of the reflected probe beam. As noted above, examples of this parameter could include the areal intensity of the beam, its full power or polarization state.

In accordance with the subject invention, a means is provided for blocking light reflected from the surface of the sample beyond a predetermined distance from the center of the focused spot. This means includes a relay lens in front of the detector for imaging and magnifying the beam. A blocking member or spatial filter is also located in front of the detector and in the focal plane of the relay lens. The blocking member includes an aperture dimensioned to block the desired amount of stray or scattered light.

The size of the area which is filtered is dependent on the magnification power of the relay lens and the size of the aperture. In practice, when the detector is arranged to measure the full power of the beam, the lens power and aperture size should be selected to block substantially all of the light that has been reflected from the sample beyond the focused spot. In contrast, where interference effects must be monitored, a larger image area should be selected. Nonetheless, some spatial filtering is still desirable to avoid measurement errors.

In the preferred embodiment, a detector is provided to monitor the power of the incident probe beam for normalizing the measurements made by the other detectors. As will be discussed below, an additional aperature should be provided in front of the incident power detector to insure that the power reaching the detector matches the power transmitted through the aperture of the microscope objective.

Further objects an advantages of the subject invention will become apparent from the following detailed description taken in conjunction with the drawings in which:

DETAILED DESCRIPTION OF THE PREFERRED EMBODIMENTS

Figure 1:
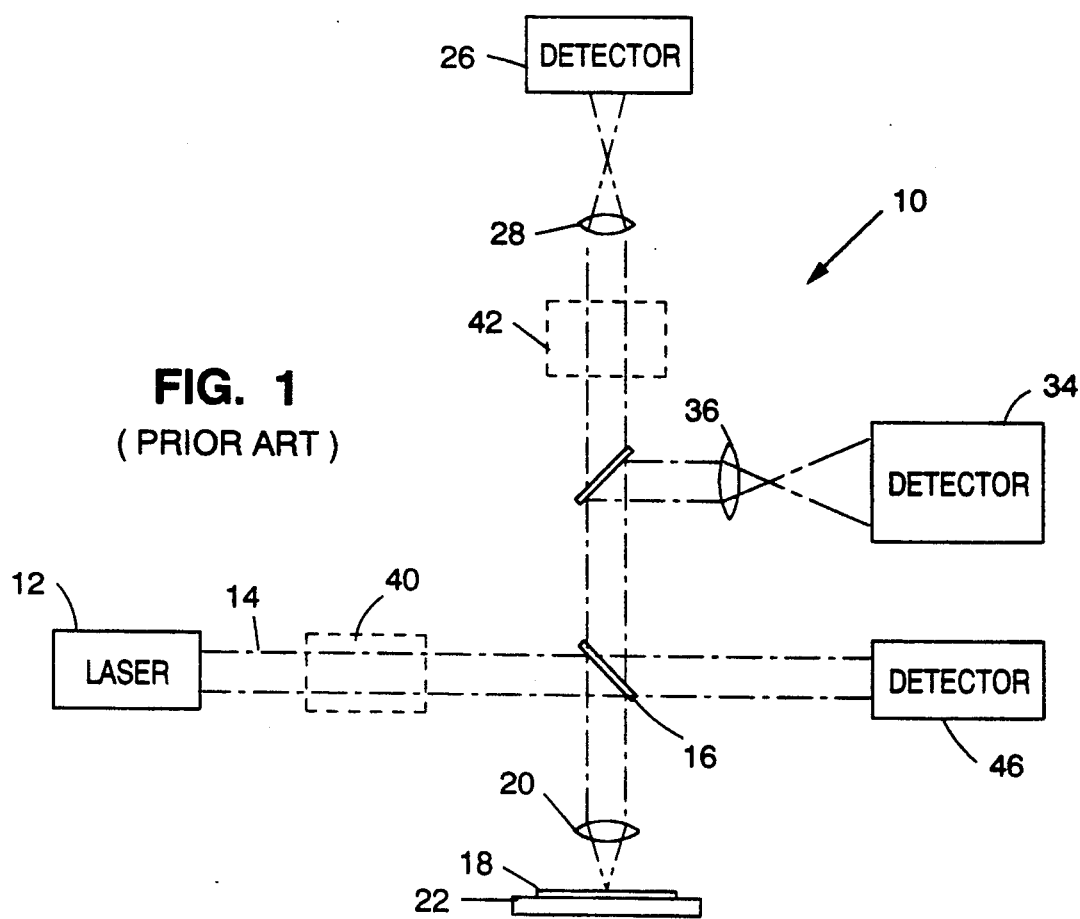
FIG. 1 is a schematic diagram of an optical measurement device of the prior art in which the subject invention can be implemented.
Figure 2:
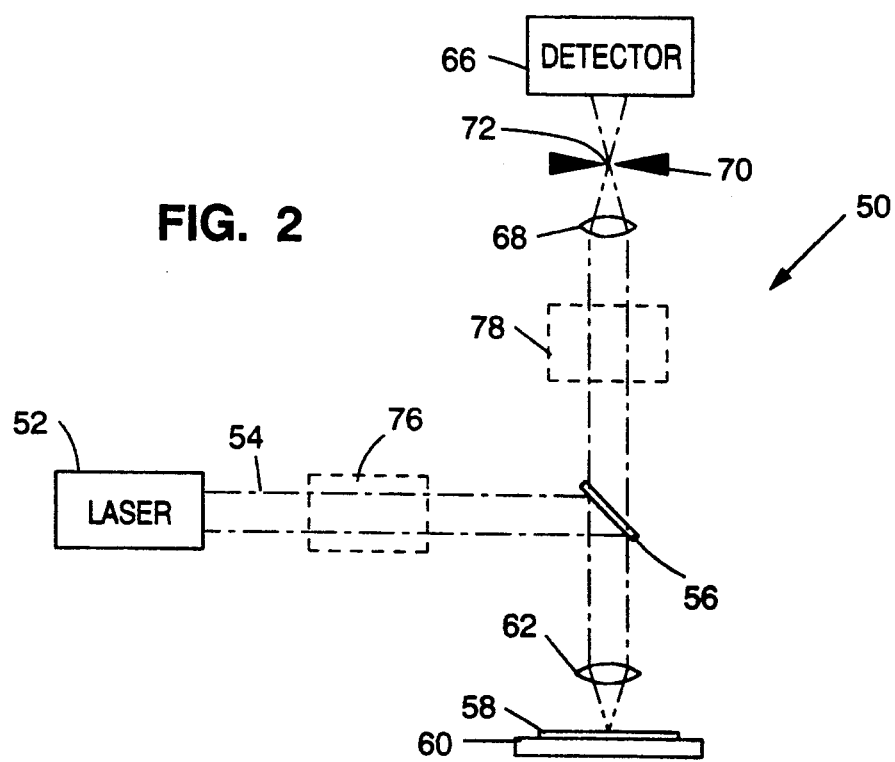
FIG. 2 is a schematic diagram of an optical measurement device in which the subject invention has been employed.

Turning to FIG. 2, there is illustrated a basic optical measurement apparatus 50 in which the principal invention of the subject application has been employed. Measurement apparatus 50 includes a laser 52 for generating a probe beam 54. A beam splitter 56 functions to redirect the beam towards the surface of the sample 58. Sample 58 rests on a movable stage 60.

Probe beam 54 is focused on the surface of the sample through a high numerical aperture lens 62 to a spot size on the order of one micron in diameter. The stage 60 allows the probe beam to be scanned relative to the surface of the sample.

A portion of the reflected probe beam travels back up through beam splitter 56 towards photodetector 66. Photodetector 66 is arranged to measure at least one parameter of the reflected probe beam.

In accordance with the subject invention, a relay lens 68 is provided to magnify and image the sample in the focal plane of the lens 68. The extent of the magnification of the image is given by the ratio of the focal length of lens 68 divided by the focal length of lens 62. In the preferred embodiment, this ratio is typically about 60 so that the image of the focused spot in this plane is about 60 microns in diameter.

In accordance with the subject invention, a blocking member 70 is located in the focal plane of the relay lens 68. Blocking member 70 includes an aperture 72 to define a spatial filter. The aperture 72 is dimensioned such that it will only transmit a portion of the relayed sample image. The amount of the image that is transmitted is defined by the size of the aperture divided by the magnification of the image. If it is desirable to substantially filter the image, an aperture of 400 microns could be used. This size aperture will reduce the filtered image field to about seven microns. In contrast, if the aperture were sized at 1500 microns, the image field would be about 24 microns in diameter.

The use of the relay lens and blocking member substantially filter any spurious laser light that is scattered by either the optics of the system or the sample itself. This result is achieved because only light that is substantially spatially coherent will enter lens 68 and will be focused through the aperture 72. Any scattered light which is not traveling substantially parallel to the axis of the lens will strike portions of the blocking member and will not be transmitted through the aperture.

As will be discussed with reference to FIG. 3, photodetector 66 can be arranged to measure either the areal intensity or the full power of the beam. The photodetector 66 can also be used in an ellipsometer device. As described in U.S. Pat. No. 5,042,951 cited above, an ellipsometer will also include a polarizing section 76 (shown in phantom line) and an analyzing section 78 (also shown in phantom line). The polarizing and analyzing sections will include polarizing elements which can be rotated about the propagation axis of the beam. By knowing the relative azimuthal positions of these rotatable elements in conjunction with the intensity measurement of detector 66, the change in polarization state of the beam can be determined. The use of a spatial filter in an ellipsometer will improve accuracy by reducing the detection of spurious light scattered from the sample.

Figure 3:
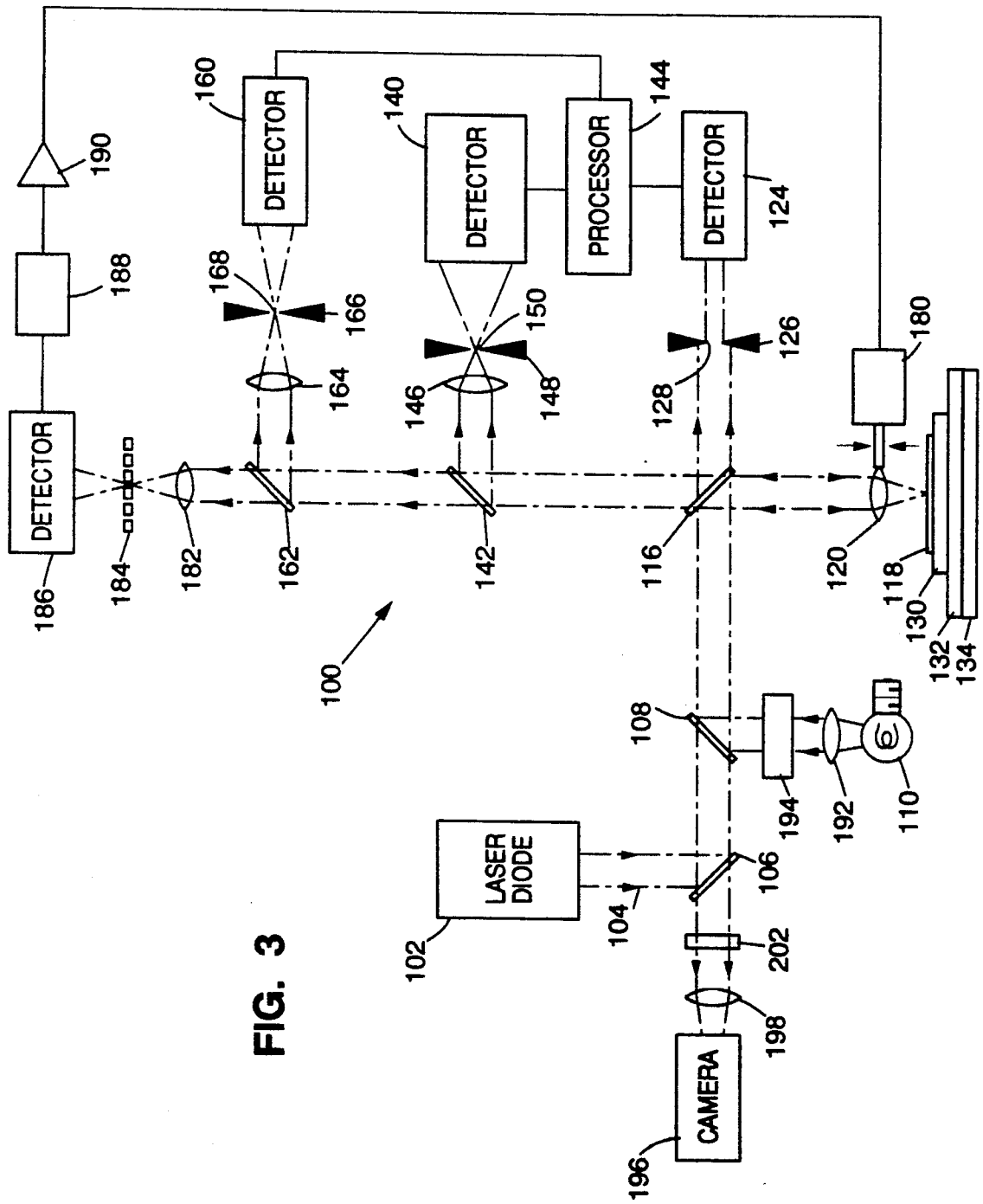
FIG. 3 is a schematic diagram of an optical measurement apparatus configured for measuring the thickness of thin films which includes the subject invention.

FIG. 3 is a schematic diagram illustrating the subject invention implemented in an apparatus 100 for measuring the thickness of thin films. This device is substantially similar to that described in our above cited U.S. Pat. No. 4,999,014. In addition to the use of spatial filters, this device includes some other modifications which have been developed since the filing of the latter patent application.

Once of the principle modifications relates to the change in the source of the probe beam. In the prior application, the suggested source was a helium-neon gas laser. In this embodiment, the laser source 102 is solid state diode laser which emits a linearly polarized beam 104. In the preferred embodiment, a Toshiba laser diode, TLD 9211, is used having a 3 milliwatt power output at 670 nm.

One advantage to using a diode laser is increased lifetime. Another significant advantage is that the coherence length is significantly shorter than a helium neon laser. Since the coherence length is shorter and therefore the divergence of the beam is greater, a much smaller percentage of the light reflected back towards the laser from the sample will enter the laser. Also, the reflected light will be less coherent when it enters the laser diode, thereby reducing optical feedback into the diode laser. Accordingly, it is unnecessary to use the more complicated filtering schemes described in the prior application and designed to prevent feedback that would cause instabilities in the laser. The remaining components in the apparatus are similar and include an imaging system, an angular sensitive photodetector, a full power detector, an incident power detector and an autofocus system.

Probe beam 104 from the laser diode is turned with a 50/50 beam splitter 106. The beam 104 is then passed through a second 50/50 beam splitter 108 which is used to combine the beam with white light from source 110. The white light is used to image the sample using a vision system described in greater detail below.

The probe beam 104 is then directed downwardly towards the sample by a 50/50 beam splitter 116 which also turns the white light down towards the sample. Upon return from the sample, part of the probe beam passes up through splitter 116 and will be measured by the detectors. Some of the white light from source 110 will be reflected back to the camera 196 of the vision system.

The probe beam 104 is focused on the sample 118 to a spot size on the order of one micron through a high numerical aperture lens 120. Lens 120 is defined by a multielement microscope objective which has a focal length of 2.25 mm and includes an internal limiting aperture four millimeters in diameter. The lens has a high numerical aperture, preferably 0.95 NA, so the various rays in the focused beam will have a wide cone angle and a large spread of angles of incidence with respect to the sample surface. As described in our copending application, the accuracy of the evaluation of layer can be enhanced by maximizing the spread of angles of incidence that are available.

In order to maximize the spread of angles of incidence, as much as possible of the working area or aperture of microscope objective 120 should be utilized. In the preferred embodiment, this result is achieved by using a probe beam diameter of about eight millimeters thereby overfilling the four millimeter aperture of the objective 120.

Another advantage that is gained from overfilling lens 120 is that the light energy at the radially outer portion of the beam 104 is not used. Since the beam typically has a gaussian-like energy distribution, the energy in the radially outer portion thereof tends to fall off and be less uniform with respect to the rest of the beam.

As noted above, since the output of laser 102 will vary somewhat, it is necessary to monitor that power in order to normalize the measurements made by the other detectors. Accordingly, the fraction of the beam that passes through beam splitter 116 is monitored by detector 124.

The fact that the lens 120 is overfilled has implications for the monitoring of the probe beam power performed by photodetector 124. More particularly, the light falling on the detector 124 should be directly related to the light which is focused on the sample. Therefore, in accordance with the subject invention, a blocking member 126 is placed in front of detector 124. The blocking member has an aperture 128 dimensioned to match the aperture in microscope objective 120. In this manner, the beam which passes through aperture 128 is the same portion of the beam which passes through the aperture of the lens 120 and back from the sample 118 to the other detectors.

The sample 118 rests on a stage which provides X, Y, and rotational positional movement. The top stage 130 provides rotational movement as well as a vacuum chuck for holding down the sample. Stages 132 and 134 provide X and Y linear movement.

A portion of the reflected probe beam 104 strikes 50/50 beam splitter 142 and is redirected to detector 140. As described above, detector 140 includes an array of individual elements capable of measuring the areal intensity of various rays as a function of their position within the reflected probe beam. The position of the rays within the beam correspond to specific angles of incidence with respect to the surface of the sample. A processor 144 derives the thickness of the thin film layer based on the angular dependent intensity measurements. As noted above, these measurements are normalized by the output of detector 124.

In accordance with the subject invention, the amount of light scattered from the sample surface which reaches the detector is reduced using a spatial filter arrangement. The spatial filter arrangement includes a relay lens 146 having a focal length of 140 mm. Relay lens 146 functions to magnify the image of the sample surface by a factor of about 60 in the image plane of the lens.

A blocking member 148 is located in the image plane of lens 146 and includes an aperture 150 that is 1500 microns in diameter. Blocking member 148 can be defined by a metal plate having a thickness of two mils. This aperture will pass a 24 micron portion of the image of the sample and restrict any light scattered from areas on the sample outside of that range. This aperature size is preferable for detector 140 since interference effects created when the beam interacts with the thin film layer contain spatial information which must pass through this spatial filter aperature. The aperature is optimized to pass enough spatial information, but filter stray light from the sample.

As noted above, in the preferred embodiment, a measurement of the full power of reflected probe beam is made. Photodetector 160 is provided for that purpose. The output of detector 160 is normalized by the processor 144 and used to enhance the accuracy of the evaluation. A portion of the reflected probe beam is directed towards detector 160 by 50/50 beam splitter 162. The beam is arranged to underfill detector 160.

In accordance with the subject invention, a spatial filter is provided consisting of relay lens 64 and blocking member 166 located in the focal plane of the lens. Like relay lens 146, lens 164 has focal length of 140 mm and functions to magnify the image by a factor of about 60. Blocking member 166 includes an aperture 168 that is 400 microns in diameter and functions to reduce the image field down to about seven microns. In this manner, virtually no light which has been reflected from areas outside the focused spot will reach the detector. Accordingly, variations recorded by the detector, which can be as small as 1 in 10,000, can be attributed to the characteristics of the sample within the focused probe beam spot.

In the preferred embodiment, an autofocus mechanism is used to maintain the spacing between the lens 120 and the sample 118 to be equal to the focal length of the lens. This distance can be maintained to less than one hundredth of a micron.

The autofocus mechanism includes a servo motor 180 for varying the vertical position of the lens 120. The servo is driven by an analog detection loop which determines if the lens 120 is properly focusing the probe beam. As seen in FIG. 3, a portion of the probe beam is transmitted by splitter 162 and is focused by a lens 182 through a chopper wheel 184 located in the focal plane of the lens. The light passing the chopper wheel 184 is imaged on a split-cell photodetector 186. If the lens 120 is out of focus, there will be a phase difference in the light striking the two sides of the split cell 186 which is detected by a phase detector 188. The phase difference is used as an input to an amplifier 190 which in turn drives the servo 180. This approach to autofocusing is known as the automated Foucault knife edge focus test.

In the preferred embodiment, a vision system is provided to allow the operator to locate areas of interest on the sample. As noted above, the vision system includes a white light source 110 which is directed to beam splitter 108 through a collimating lens 192. A mechanical shutter 194 for selectively blocking the light source is provided. In operation, shutter 194 is closed during measurement periods so that the white light will not reach any of the photodetectors. In this manner, the accuracy of the measurement can be enhanced by further reducing any spurious light.

Some of the white light that has been directed down to the sample by splitter 116 will be reflected back along the same path passing through 50/50 splitters 108 and 106 to reach video camera 196. A lens 198 focuses the image provided to the camera. A variable laser wavelength cut-off filter 202 is provided to control the amount of probe beam light falling on the video camera. A more detailed explanation of the steps taken by the processor 144 to derive layer thickness is given in our copending application.

In summary there has been disclosed an approach for increasing the sensitivity of a high resolution measurement device. The device includes a laser for generating a probe beam which is tightly focused onto the surface of the sample. A detector is provided for monitoring a parameter of the reflected probe beam. In accordance with the subject invention, a spatial filter is provided for reducing the amount of light energy reaching the detector that has been reflected from areas on the surface of the sample beyond the focused spot. The spatial filter includes a relay lens and a blocking member located in the focal plane of the relay lens. The blocking member includes an aperture dimensioned to block light reflected from the surface of the sample beyond a predetermined distance from the center of the focused spot. In this manner, greater sensitivity to sample characteristics within the highly focused spot is achieved.

While the subject invention has been described with reference to preferred embodiments, various changes and modifications could be made therein, by one skilled in the art, without varying from the scope and spirit of the subject invention as defined by the appended claims.

I claim:

1. A measurement apparatus for evaluating the optical properties of a thin film layer formed on the surface of a sample comprising:
   laser means for generating a probe beam;
   primary lens means for focusing the probe beam to a spot on the surface of the sample;
   detector means for measuring the reflected probe beam and generating an output signal for evaluating the sample;
   relay lens means located in front of the detector means; and
   blocking means located between said detector means and said relay lens means and in the focal plane of the relay lens means, said blocking means having an aperture dimensioned to transmit focused light reflecting off the boundaries of the thin film layer and block scattered light reflected form the surface of the sample beyond a predetermined distance from the center of the focused spot.

2. An apparatus as recited in claim 1 wherein said primary lens means focuses the probe beam to a spot size on the order of one micron in diameter.

3. An apparatus as recited in claim 2 wherein said detector means measures the areal intensity of the reflected probe beam.

4. An apparatus as recited in claim 2 wherein said detector means measurers the power of the reflected probe beam.

5. An apparatus as recited in claim 2 wherein said detector means measures the polarization state of the reflected probe beam.

6. An apparatus as recited in claim 2 wherein said predetermined distance is 12 microns or less.

7. An apparatus as recited in claim 2 wherein said predetermined distance is equal to about four microns.

8. An apparatus for evaluating optical parameters of a thin film layer formed on the surface of a sample comprising:
   laser means for generating a probe beam;
   primary lens means for focusing the probe beam to a spot size on the order of micron in diameter on the surface of the sample;
   first detector means for measuring the full power of the reflected probe beam;
   first relay lens means located in front of the detector means; and
   first blocking means located between said detector means and said first relay lens means and in the focal plane of the first relay lens means, said first blocking means having an aperture dimensioned to transmit focused light reflecting off the boundaries of the thin film layer and block scattered light reflected from the surface of the sample beyond a first predetermined distance from the center of the focused spot.

9. An apparatus as recited in claim 8 wherein said predetermined distance is 12 microns or less.

10. An apparatus as recited in claim 8 wherein said predetermined distance is equal to about four microns.

11. An apparatus as recited in claim 8 further comprising:
    second detector means for measuring a parameter of the reflected probe beam other than its full power;
    second relay lens means located in front of the detector means; and
    second blocking means located between said second detector means and said second relay lens means and in the focal plane of the second relay lens means, said second blocking means having an aperture dimensioned to block light reflected from the surface of the sample beyond a second predetermined distance from the center of the focused spot, with said second predetermined distance being greater than the first predetermined distance.

12. An optical measurement device for evaluating a sample comprising:
    laser means for generating a probe beam;

a lens having an aperture for focusing the probe beam on the surface of the sample, and with the diameter of the probe beam in the plane of the lens being greater than the diameter of the aperture so that the lens is overfilled;

first detector means for measuring the reflected probe beam and generating a first output signal for evaluating the sample;

second detector means positioned to receive a portion of the probe beam without passing through the lens or being reflected from the sample, said second detector means for measuring the incident power of the probe beam and generating a second output signal for normalizing the first output signal; and blocking means positioned in front of the second detector means and having an aperture dimensioned in a manner to restrict the transmission of the probe beam to be equal to the transmission of the probe beam through the aperture of the lens.

13. An apparatus as recited in claim 12 further including a beam splitter positioned to direct a portion of the probe beam towards said lens and another portion to said second detector.

* * * * *